United States Patent [19]

Drabek

[11] 4,410,543
[45] Oct. 18, 1983

[54] CARBOXYLATED OXIME-CARBAMATES AND THEIR USE IN CONTROLLING PESTS

[75] Inventor: Jozef Drabek, Oberwil, Switzerland

[73] Assignee: Ciba-Geigy Corporation, Ardsley, N.Y.

[21] Appl. No.: 360,024

[22] Filed: Mar. 19, 1982

[30] Foreign Application Priority Data

Mar. 26, 1981 [CH] Switzerland .......................... 2073/81
Jan. 8, 1982 [CH] Switzerland .......................... 100/82

[51] Int. Cl.³ .................. A01N 47/22; C07D 307/86; C07C 153/00
[52] U.S. Cl. ..................................... 424/278; 424/283; 424/285; 424/300; 549/370; 549/448; 549/470; 260/353.3
[58] Field of Search ..................... 549/470, 370, 448; 260/453.3; 424/300, 278, 283, 285

[56] References Cited

FOREIGN PATENT DOCUMENTS 5246 11/1979 European Pat. Off. .

*Primary Examiner*—Alan L. Rotman
*Assistant Examiner*—Bernard Dentz
*Attorney, Agent, or Firm*—Frederick H. Rabin

[57] ABSTRACT

Carboxylated oxime-carbamates of the formula

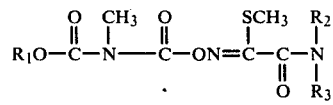

in which $R_1$ represents a substituted or unsubstituted phenyl, naphthyl or dihydrobenzofuranyl radical and $R_2$ and $R_3$ independently of one another represent hydrogen or $C_1$–$C_4$-alkyl.

A process for the preparation of these carboxylated oxime-carbamates, and their use in controlling pests, are described.

10 Claims, No Drawings

CARBOXYLATED OXIME-CARBAMATES AND THEIR USE IN CONTROLLING PESTS

The present invention relates to carboxylated oxime-carbamates, a process for their preparation, and their use in controlling pests.

The carboxylated carbamates have the formula

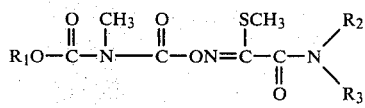

in which $R_1$ represents a substituted or unsubstituted phenyl, naphthyl or dihydrobenzofuranyl radical and $R_2$ and $R_3$ independently of one another represent hydrogen or $C_1$-$C_4$-alkyl.

Suitable substituents on the radicals falling under $R_1$ are preferably 1 to 3 halogen atoms, such as fluorine, chlorine, bromine or iodine atoms, particularly chlorine atoms, or dioxolanyl, dioxanyl, alkyl, alkenyl, alkynyl, alkoxy or alkylthio groups. The alkyl, alkenyl, alkynyl, alkoxy and alkylthio groups can be straight-chain or branched, and can be unsubstituted or substituted by halogen and/or alkoxy, and preferably have 1 to 6, or 2 to 6, respectively, carbon atoms in the chain. Examples of such groups are, inter alia: methyl, methoxy, methylthio, ethyl, ethoxy, 1-methoxy-2-chloroethoxy, 1-methoxymethylethoxy, ethylthio, propyl, propoxy, isopropyl, isopropoxy, n-, i-, sec.- or tert.-butyl, n-pentyl, n-hexyl, vinyl, allyl, ethinyl and propargyl.

In the case of $R_2$ and $R_3$, the alkyl groups are methyl, ethyl, propyl, isopropyl, n-, i-, sec.- and tert.-butyl, but particularly methyl. Dioxolanyl and dioxanyl groups are to be understood as meaning groups of the formulae

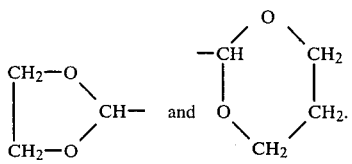

Compounds of the formula I which are preferred are those in which $R_1$ represents a substituted or unsubstituted phenyl, naphthyl or dihydrobenzofuranyl radical, and $R_2$ and $R_3$ independently of one another represent hydrogen or methyl. Compounds of the formula I which are particularly preferred are, however, those in which $R_1$ represents a substituted or unsubstituted phenyl, naphthyl or dihydrobenzofuranyl radical, and $R_2$ and $R_3$ each represent methyl. Compounds of the formula I which are especially preferred are those in which $R_1$ represents unsubstituted phenyl, naphthyl or dihydrobenzofuranyl, or phenyl, naphthyl or dihydrobenzofuranyl which is substituted by 1 to 3 fluorine, chlorine, bromine or iodine atoms or dioxolanyl, dioxanyl, alkyl, alkenyl, alkynyl, alkoxy or alkylthio groups, and $R_2$ and $R_3$ independently of one another represent hydrogen or methyl.

Compounds of the formula I which are very particularly preferred are those in which $R_1$ represents phenyl, 4-chlorophenyl, 2-(1-methoxymethylethoxy)-phenyl, 2-isopropoxyphenyl, 2-(1-methoxy-2-chloroethoxy)-phenyl, naphthyl or 2,2-dimethyl-2,3-dihydrobenzofuranyl, and $R_2$ and $R_3$ each represent methyl.

Of these, special mention should be made of compounds of the formula I in which $R_1$ represents unsubstituted phenyl, 4-chlorophenyl, naphthyl or 2,2-dimethyl-2,3-dihydrobenzofuranyl, and $R_2$ and $R_3$ each represent methyl.

The compounds of the formula I can be prepared by methods which are known per se, for example as follows:

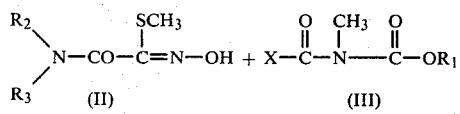

In the formulae II and III, $R_1$, $R_2$ and $R_3$ are as defined in formula I and X represents a halogen atom, in particular fluorine or chlorine.

The process is carried out at a reaction temperature between $-50°$ C. and $+130°$ C., preferably between $-10°$ C. and $+100°$ C., under normal or slightly elevated pressure and in the presence of a base and, if desired, in the presence of a solvent or diluent which is inert towards the reactants.

Bases which are suitable for this process are, in particular, tertiary amines, such as trialkylamines, pyridines and dialkylanilines, and also hydroxides, oxides, carbonates and bicarbonates of alkali and alkaline earth metals, and also alkali metal alcoholates, for example potassium tert.-butylate or sodium methylate.

Examples of suitable solvents or diluents are ethers and ether-like compounds, such as diethyl ether, diisopropyl ether, dioxane or tetrahydrofuran; aliphatic and aromatic hydrocarbons, in particular benzene, toluene or xylenes; and ketones, such as acetone, methyl ethyl ketone and cyclohexanone.

The starting materials of the formulae II and III are known or can be prepared analogously to known methods.

The compounds of the formula I are suitable for controlling pests on animals and plants.

In particular, the compounds of the formula I are suitable for controlling insects, for example those of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and hymenoptera, and phytopathogenic mites and ticks of the orther Acarina.

In particular, compounds of the formula I are suitable for controlling insects which damage plants, in particular eating insects which damage plants in ornamental and useful plants, particularly incotton crops (for example *Spodoptera littoralis* and *Heliothis virescens*) and vegetable crops (for example *Leptinotarsa decemlineata* and *Myzus persicae*).

It should be emphasised in this connection that the said compounds are distinguished by both a strongly pronounced systemic action and a contact action against sucking insects, in particular against sucking insects of the order Homoptera and, in particular, against insects of the family Aphididae (for example *Aphis fabae, Aphis craccivora* and *Myzus persicae*), which can only be controlled with difficulty using known compositions.

Active compounds of the formula I also show a very advantageous action against flies, for example *Musca*

*domestica*, and mosquito larvae. They are also distinguished by a broad ovicidal and ovilarvicidal action, and possess a valuable action against ectoparasitic mites and ticks, for example those of the families Ixodidae, Argasidae and Dermanyssidae.

The compounds of the formula I are employed in an unaltered form or, preferably, together with the assistants conventionally used in the art of formulation, and are therefore processed in a known manner to give, for example, emulsion concentrates, solutions which can be directly atomised or diluted, dilute emulsions, wettable powders, soluble powders, dusts, granules or encapsulations in, for example, polymeric materials. The application processes, such as atomisation, nebulisation, dusting, sprinkling or watering are selected to suit the intended aims and given circumstances, as is the nature of the composition.

The formulations, i.e. the compositions, preparations or combinations containing the active compound of the formula I and, if desired, a solid or liquid adjuvant, are prepared in a known manner, for example by intimately mixing and/or grinding the active compounds with diluents, for example solvents, solid carriers and, if desired, surface-active compounds (tensides).

The following are possible solvents: aromatic hydrocarbons, preferably the $C_8$ to $C_{12}$ fractions, for example mixed xylenes or substituted naphthalenes, phthalic acid esters, such as dibutyl or dioctyl phthalate, aliphatic hydrocarbons, such as cyclohexane or paraffins, alcohols and glycols and also ethers and esters thereof, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide and also epoxidised or non-epoxidised vegetable oils, such as epoxidised coconut oil or soya oil; or water.

As a rule, natural ground minerals, such as calcite, talc, kaolin, montmorillonite or attapulgite, are used as solid carriers, for example for dusts and dispersible powders. Highly disperse silica or highly disperse absorbent polymers can also be added in order to improve the physical properties. Possible particulate, adsorptive granular carriers are porous types, such as pumice stone, broken brick, sepiolite or bentonite, while examples of possible non-sorptive carrier materials are calcite or sand. In addition, it is possible to use a large number of pregranulated materials of an inorganic or organic nature, such as, in particular, dolomite or comminuted plant residues.

Depending on the nature of the active compound of the formula I to be formulated, suitable surface-active compounds are nonionic, cationic and/or anionic tensides which have good emulsifying, dispersing and wetting properties. Tensides are also to be understood as meaning mixtures of tensides.

Suitable anionic tensides can be so-called water-soluble soaps as well as water-soluble synthetic surface-active compounds.

Suitable soaps are the alkali metal salts, alkaline earth metal salts or substituted or unsubstituted ammonium salts of higher fatty acids ($C_{10}$–$C_{22}$), for example the Na or K salts of oleic or stearic acid, or of natural mixtures of fatty acids which can be obtained, for example, from coconut oil or tallow oil. Mention should also be made of the fatty acid salts of methyltauride.

More often, however, so-called synthetic tensides are used, in particular fatty sulfonates, fatty sulfates, sulfonated benzimidazole derivatives or alkylarylsulfonates.

The fatty sulfonates or sulfates are, as a rule, in the form of alkali metal salts, alkaline earth metal salts or substituted or unsubstituted ammonium salts, and contain an alkyl radical having 8 to 22 C atoms, in which connection alkyl also includes the alkyl moiety of acyl radicals, for example the Na or Ca salt of ligninsulfonic acid, of dodecylsulfuric acid ester or of a mixture of fatty alcohol sulfates prepared from natural fatty acids. These also include the salts of the sulfuric acid esters and sulfonic acids of fatty alcohol/ethylene oxide adducts. The sulfonated benzimidazole derivatives preferably contain 2 sulfonic acid groups and a fatty acid radical having 8–22 C atoms. Examples of alkylarylsulfonates are the Na, Ca or triethanolamine salts of dodecylbenzylsulfonic acid, of dibutylnaphthalenesulfonic acid or of a naphthalenesulfonic acid/formaldehyde condensation product.

Furthermore, corresponding phosphates, for example salts of the phosphoric acid ester of a p-nonylphenol/-(4–14)-ethylene oxide adduct are also possible.

Possible nonionic tensides are primarily polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Further suitable nonionic tensides are the water-soluble adducts, containing 20 to 250 ethylene glycol ether groups and 10 to 100 propylene glycol ether groups, of polyethylene oxide with polypropylene glycol, ethylenediaminopolypropylene glycol and an alkyl polypropylene glycol having 1 to 10 carbon atoms in the alkyl chain. The said compounds usually contain 1 to 5 ethylene glycol units per unit of propylene glycol.

Nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol may be mentioned as examples of nonionic tensides.

Furthermore, fatty acid esters of polyoxyethylenesorbitan, such as polyoxyethylenesorbitan trioleate, are also suitable.

Cationic tensides are, in particular, quaternary ammonium salts which contain, as the N-substituent, at least one alkyl radical having 8 to 22 C atoms, and, as further substituents, lower alkyl or benzyl radicals, which can be halogenated, or lower hydroxyalkyl radicals. The salts are preferably in the form of halides, methylsulfates or ethylsulfates, for example stearyltrimethylammonium chloride or benzyldi-(2-chloroethyl)-ethylammonium bromide.

The tensides which are customary in the art of formulation are described, inter alia, in the following publication: "McCutcheon's Detergents and Emulsifiers Annual" MC Publishing Corp., Ringwood, N.J., 1979.

As a rule, the pesticidal preparations contain 0.1 to 99%, in particular 0.1 to 95%, of an active compound of the formula I, 1 to 99% of a solid or liquid adjuvant and 0 to 25%, in particular 0.1 to 25%, of a tenside.

Whereas concentrated compositions are more likely to be preferred as commercial products, the final consumer generally uses dilute compositions.

The compositions can also contain further additives, such as stabilisers, anti-foaming agents, viscosity regulators, binders, adhesives and fertilisers or other active compounds for achieving special effects.

EXAMPLES of formulations of liquid active compounds of the formula I (%=percent by weight)

| 1. Emulsion concentrates | (a) | (b) | (c) |
|---|---|---|---|
| Active compound | 20% | 40% | 50% |
| Ca dodecylbenzenesulfonate | 5% | 8% | 5.8% |
| Castor oil polyethylene glycol ether (36 mols of EO) | 5% | — | — |
| Tributylphenyl polyethylene glycol ether (30 mols of EO) | — | 12% | 4.2% |
| Cyclohexanone | — | 15% | 20% |
| Mixed xylenes | 70% | 25% | 20% |

Emulsions of any desired concentration can be prepared from such concentrates by dilution with water.

| 2. Solutions | (a) | (b) | (c) | (d) |
|---|---|---|---|---|
| Active compound | 80% | 10% | 5% | 95% |
| Ethylene glycol monomethyl ether | 20% | — | — | — |
| Polyethylene glycol MW 400 | — | 70% | — | — |
| N—methyl-2-pyrrolidone | — | 20% | — | — |
| Epoxidised coconut oil | — | — | 1% | 5% |
| Petroleum ether (boiling range 160-190° C.) | — | — | 94% | — |

The solutions are suitable for application in the form of very fine drops.

| 3. Granules | (a) | (b) |
|---|---|---|
| Active compound | 5% | 10% |
| Kaolin | 94% | — |
| Highly disperse silica | 1% | — |
| Attapulgite | — | 90% |

The active compound is dissolved in methylene chloride, the solution is sprayed onto the carrier and the solvent is then evaporated in vacuo.

| 4. Dusts | (a) | (b) |
|---|---|---|
| Active compound | 2% | 5% |
| Highly disperse silica | 1% | 5% |
| Talc | 97% | — |
| Kaolin | — | 90% |

Ready-to-use dusts are obtained by intimately mixing the carriers with the active compound.

EXAMPLES of formulations of solid active compounds of the formula I (%=percent by weight)

| 5. Wettable powders | (a) | (b) |
|---|---|---|
| Active compound | 20% | 60% |
| Na ligninsulfonate | 5% | 5% |
| Na laurylsulfate | 3% | — |
| Na diisobutylnaphthalenesulfonate | — | 6% |
| Octylphenol polyethylene glycol ether (7-8 mols of EO) | — | 2% |
| Highly disperse silica | 5% | 27% |
| Kaolin | 67% | — |

The active compound is thoroughly mixed with the adjuvants and thoroughly ground in a suitable mill. This gives wettable powders which can be diluted with water to give suspensions of any desired concentration.

| 6. Emulsion concentrate | |
|---|---|
| Active compound | 10% |
| Octylphenol polyethylene glycol ether (4-5 mols of EO) | 3% |
| Ca dedecylbenzenesulfonate | 3% |
| Castor oil polyglycol ether (36 mols of EO) | 4% |
| Cyclohexanone | 30% |
| Mixed xylenes | 50% |

Emulsions of any desired concentration can be prepared from this concentrate by dilution with water.

| 7. Dusts | (a) | (b) |
|---|---|---|
| Active compound | 5% | 8% |
| Talc | 95% | — |
| Kaolin | — | 92% |

Ready-to-use dusts are obtained by mixing the active compound with the carrier and grinding the mixture on a suitable mill.

| 8. Extruder granules | |
|---|---|
| Active compound | 10% |
| Na ligninsulfonate | 2% |
| Carboxymethylcellulose | 1% |
| Kaolin | 87% |

The active compound is mixed with adjuvants and the mixture is ground and moistened with water. This mixture is extruded and then dried in a stream of air.

| 9. Coated granules | |
|---|---|
| Active compound | 3% |
| Polyethylene glycol (MW 200) | 3% |
| Kaolin | 94% |

The active compound is finely ground and uniformly applied, in a mixer, to the kaolin, which has been moistened with polyethylene glycol. Dust-free coated granules are obtained in this way.

| 10. Suspension concentrate | |
|---|---|
| Active compound | 40% |
| Ethylene glycol | 10% |
| Nonylphenol polyethylene glycol ether (15 mols of EO) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The active compound is finely ground and intimately mixed with the adjuvants. This gives a suspension concentrate from which suspensions of any desired concentration can be prepared by dilution with water.

EXAMPLE 1

Preparation of the compound of the formula

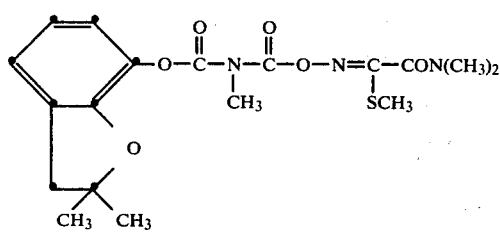

2.28 g of 2,2-dimethyl-2,3-dihydrobenzofuranyl N-chlorocarbonyl-N-methylcarbamate, dissolved in 50 ml of chloroform, are added dropwise, at 0° to 10° C., to a solution of 4.05 g of N,N-dimethyl-2-oximino-2-(methylthio)acetamide in 100 ml of 1:1 toluene/acetonitrile containing 5.5 ml of triethylamine and 0.2 g of 4-dimethylaminopyridine. The reaction mixture is stirred for 12 hours at 20° C. and for 5 hours under reflux. After the mixture has been concentrated, the residue is taken up in toluene. After being filtered with suction, the toluene solution is washed twice with 100 ml of water, with 100 ml of 1 N hydrochloric acid solution and with 100 ml of 1 N bicarbonate solution, and is dried over sodium sulfate and concentrated.

This gives the compound of the title, which has a refractive index $n_D^{50°}$ of 1.5382.

The following compounds are also prepared in an analogous manner:

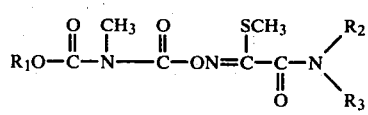

| No. | R$_1$ | R$_2$ | R$_3$ | Physical data |
|---|---|---|---|---|
| 2 | (2,3-dihydrobenzofuranyl) | CH$_3$ | CH$_3$ | $n_D^{50°} = 1.5933$ |
| 3 | (benzofuranyl) | CH$_3$ | CH$_3$ | $n_D^{20°} = 1.5408$ |
| 4 | Cl-(benzofuranyl) | CH$_3$ | CH$_3$ | $n_D^{20°} = 1.5570$ |
| 5 | (furanyl-O-CH(CH$_3$)-CH$_2$OCH$_3$) | CH$_3$ | CH$_3$ | $n_D^{20°} = 1.5376$ |
| 6 | (furanyl-O-CH(CH$_3$)$_2$) | CH$_3$ | CH$_3$ | $n_D^{20°} = 1.5408$ |
| 7 | (furanyl-O-CH(OCH$_3$)-CH$_2$Cl) | CH$_3$ | CH$_3$ | $n_D^{50°} = 1.5477$ |
| 8 | (2,2-dimethyl-2,3-dihydrobenzofuranyl) | H | H | m.p.: 150–151° C. |
| 9 | CF$_3$-phenyl | CH$_3$ | CH$_3$ | $n_D^{50°} = 1.5142$ |
| 10 | Cl,Cl-phenyl | CH$_3$ | CH$_3$ | m.p.: 136–138° C. |

EXAMPLE 2

Insecticidal systemic action: *Aphis craccivora*

Bean plants which have rooted are transplanted into pots containing 600 ccm of soil. 50 ml of a test solution containing 25 ppm, 5 ppm or 1 ppm of the compound to be tested are then poured straight onto the soil.

After 24 hours, aphids (*Aphis craccivora*) are placed on the parts of the plants above ground, and a plastic cylinder which is laced up underneath is turned over the plants in order to protect the aphids from possible contact action or gas action of the test substance.

The mortality achieved is evaluated 48 hours after the start of the test. Two plants, each in a separate pot, are used for each concentration dose of test substance. The test is carried out at 25° C. and 70% relative atmospheric humidity.

The action of the compounds according to Example 1 against *Aphis craccivora* is shown in the table below.

Results of biological tests

The results of tests based on the above example are listed in the table which follows, in which the following rating index refers to the percentage mortality of the pests:

A: 70–100% mortality at a concentration of active compound of 1 ppm
B: 70–100% mortality at a concentration of active compound of 5 ppm
C: 70–100% mortality at a concentration of active compound of 25 ppm.

| Compound No. | Activity against *Aphis craccivora* |
|---|---|
| 1 | A |
| 2 | B |
| 3 | B |
| 4 | A |
| 5 | A |
| 6 | A |

-continued

| Compound No. | Activity against *Aphis craccivora* |
|---|---|
| 7 | B |
| 8 | C |
| 9 | B |
| 10 | A |

What is claimed is:

1. A carboxylated oxime-carbamate of the formula $$R_1O-\overset{O}{\underset{\|}{C}}-\overset{CH_3}{\underset{|}{N}}-\overset{O}{\underset{\|}{C}}-ON=\overset{SCH_3}{\underset{|}{C}}-\overset{}{\underset{\|}{\underset{O}{C}}}-N\overset{R_2}{\underset{R_3}{\diagdown}}$$

in which $R_1$ represents phenyl, naphthyl or dihydrobenzofuranyl, optionally substituted by halogen, dioxolanyl, dioxanyl, $C_1$-$C_6$-alkyl, $C_2$-$C_6$-alkenyl, $C_2$-$C_6$-alkynyl, $C_1$-$C_6$ alkoxy or $C_1$-$C_6$-alkylthio, the alkyl, alkenyl, alkynyl, alkoxy and alkylthio groups themselves optionally substituted by halogen or $C_1$-$C_6$-alkoxy, and $R_2$ and $R_3$ independently of one another represent hydrogen or $C_1$-$C_4$-alkyl.

2. A compound according to claim 1, in which $R_2$ and $R_3$ independently of one another represent hydrogen or methyl.

3. A compound according to claim 1 or 2, in which $R_2$ and $R_3$ each represent methyl.

4. A compound according to claim 2, in which $R_1$ represents unsubstituted phenyl, naphthyl or dihydrobenzofuranyl, or phenyl, naphthyl or dihydrobenzofuranyl which is substituted by 1 to 3 fluorine, chlorine, bromine or iodine atoms or dioxolanyl, dioxanyl, alkyl, alkenyl, alkynyl, alkoxy or alkylthio groups.

5. A compound according to claim 4, in which $R_1$ represents phenyl, 4-chlorophenyl, 2-(2-methoxymethylethoxy)-phenyl, 2-isopropoxyphenyl, 2-(1-methoxy-2-chloroethoxy)-phenyl, 3-trifluoromethylphenyl, 3,4-dichlorophenyl, naphthyl or 2,2-dimethyl-2,3-dihydrobenzofuranyl and $R_2$ and $R_3$ each represent methyl.

6. A compound according to claim 5, in which $R_1$ represents phenyl, 4-chlorophenyl, naphthyl or 2,2-dimethyl-2,3-dihydrobenzofuranyl.

7. The compound, according to claim 6, of the formula

8. The compound, according to claim 6, of the formula

9. An insecticidal and acaricidal composition which comprises (1), as the active component, an insecticidally or acaricidally effective amount of a compound according to claim 1, and (2) a carrier.

10. A method of combatting pests of the class Insecta or of the order Acarina at a locus, which method comprises applying to the locus an insecticidally or acaricidally effective amount of a compound as claimed in claim 1.

* * * * *